US008776612B2

(12) United States Patent
Zampieri et al.

(10) Patent No.: US 8,776,612 B2
(45) Date of Patent: Jul. 15, 2014

(54) METHOD FOR DETERMINING THE DYNAMIC CHARACTERISTICS OF A SKI BOOT

(75) Inventors: Claudio Fortunato Zampieri, Tombolo (IT); Fernando De Cassan, Preganziol (IT); Franco Ferrarese, Treviso (IT); Alfred Pellegrini, Montebelluna (IT)

(73) Assignee: Tecnica Group S.p.A., Giavera del Montello (IT)

( * ) Notice: Subject to any disclaimer, the term of this patent is extended or adjusted under 35 U.S.C. 154(b) by 203 days.

(21) Appl. No.: 13/354,694

(22) Filed: Jan. 20, 2012

(65) Prior Publication Data

US 2012/0198942 A1 Aug. 9, 2012

(30) Foreign Application Priority Data

Feb. 3, 2011 (IT) ............................... PN2011A0005

(51) Int. Cl.
*G01N 3/20* (2006.01)
(52) U.S. Cl.
USPC ............................................................ 73/849
(58) Field of Classification Search
USPC ............................................................ 73/849
See application file for complete search history.

*Primary Examiner* — Lisa Caputo
*Assistant Examiner* — Jonathan Dunlap
(74) *Attorney, Agent, or Firm* — Oblon, Spivak, McClelland, Maier & Neustadt, L.L.P.

(57) ABSTRACT

The present invention refers to a method for determining the dynamic characteristics of a ski boot comprising the steps of selecting at least three parameters suitable to represent some dynamic characteristics of the boot, experimentally determining the values assumed from each of the parameters, and finally determining the dynamic behavior of the ski boot on the basis of the combination of the values measured in the previous step. Also claimed is an apparatus for determining a parameter of dynamic behavior of a ski boot.

15 Claims, 3 Drawing Sheets

METHOD FOR DETERMINING THE DYNAMIC CHARACTERISTICS OF A SKI BOOT

The present invention refers to a method for determining the parameters relative to some dynamic characteristics of a ski boot, whose combined values define its dynamic behaviour. The present invention also refers to an apparatus for determining one of said parameters.

Generally, the performance characteristics of the ski boots are evaluated by means of a commercial index, referred to as the "FLEX" index, expressed by a number between 50 and 150 that substantially defines the force to apply to the upper shell to bend it forward with respect to the lower shell; for example, a boot with a "FLEX" index of 150 is considered stiff, suitable in particular for some skiing disciplines or competitions, while a boot with a "FLEX" of 50 is considered pliable and suitable for a beginner.

The "FLEX" index is correlated with an experimental parameter, that can be determined in the laboratory through the use of a known testing apparatus that measures the force exerted on a mechanical arm connected to a prosthesis inserted into the boot to be tested so that the same prosthesis bends forward by a certain angle, conventionally assumed as 10°.

The temperature at which the test is carried out is −5°, in order to take into account the natural stiffening of the materials making up the boot in the normal conditions of use, that is, at low temperatures.

If until recently the "FLEX" index was sufficient to classify the boots present on the market, with the arrival and evolution of new skiing disciplines, very different from each other and practised by beginners as well as professionals, there is an increasing need to differentiate the boots on the basis of the performance required for each application.

Hence, given the wide range of boots available on the market, the "FLEX" parameter alone is no longer sufficient to describe all the different dynamic behaviours.

The main objective of the subject matter of the present invention is to overcome the drawbacks of the known art by devising a method for determining the dynamic characteristics of a ski boot based on three new parameters measured through suitable experimental tests that, on one hand make it possible to draw up a detailed classification that enables the users to look for the most suitable boot on the basis of their skill and their skiing discipline, and that on the other hand gives manufacturers a testing instrument to determine on the prototype if the new boot designs have the dynamic characteristics suitable for the skiing discipline for which they were designed.

In the scope of the above-mentioned objective, one purpose of the present invention is to provide a method based on three reference parameters that can be univocally determined through easily repeatable measurements.

Another purpose of the invention is to express through the three chosen parameters some intuitive concepts that enable the user to instantly identify the type of boot desired.

The objective and the purposes indicated above, and others that will be better disclosed hereafter, are achieved through the implementation of a method for determining the dynamic characteristics of a boot as defined in claim 1, in which one of the parameters used as an indicator is determined by means of an apparatus as defined in claim 13.

Advantages and characteristics of the invention will become evident from the following description, given by way of non-limiting example, with reference to the enclosed drawings, wherein.

Figure 1:
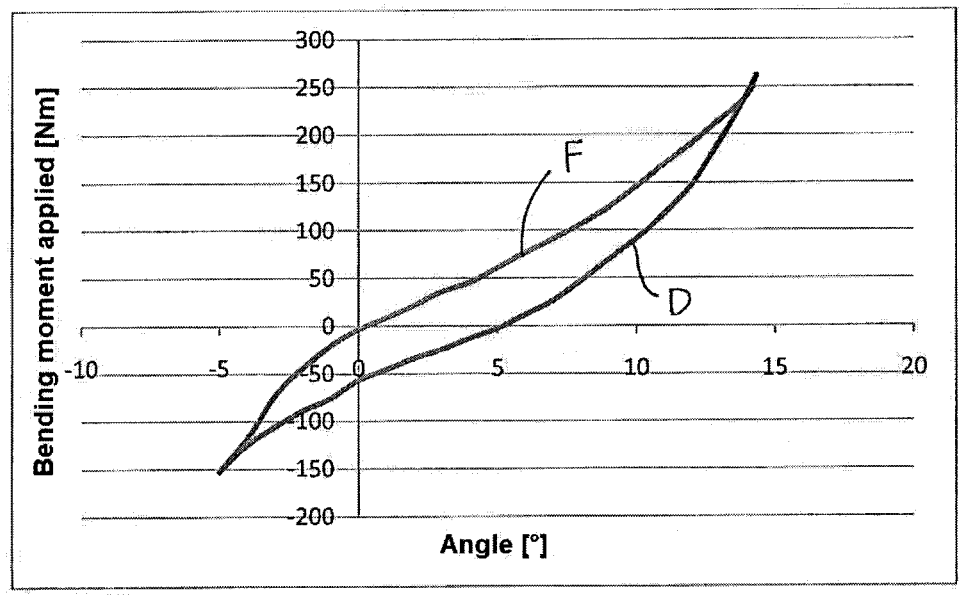
FIGS. 1 and 2 illustrate graphs from a test cycle for measuring some parameters for the dynamic characterization of a boot according to the present invention.

As mentioned above, in recent years, with the arrival and evolution of new winter sports disciplines, the use of single parameter as an indicator of the dynamic properties has shown itself to be insufficient for characterizing the wide variety of boots present on the market and meeting each of the specific performance requirements for each discipline.

This has given rise to the need to identify new parameters capable of more accurately representing, if combined together, the dynamic behaviour or the boots. Among the various parameters considered, three in particular have proven to be more suitable to provide a detailed picture of the different types of boots present on the market.

Specifically, the three parameters that have been selected for the dynamic characterization of a boot from all those considered are: stiffness S, progression P and rebound R. Obviously, other parameters that represent the dynamic characteristics of a boot can be used, without thereby departing from the scope of patent protection defined by claim 1.

Stiffness S is a parameter that expresses the bending moment necessary to bend the upper shell forward at a first given angle relative to the lower shell.

Progression P is a parameter that expresses the increase in stiffness during a forward bending cycle from a neutral position to a maximum bending position.

Finally, the rebound R is a parameter that expresses the speed at which the upper shell returns to the neutral position from the maximum bending position.

The first two parameters S, P are preferably determined through the use of a known apparatus, referred to as "SWT Giuliani", that is the same device hitherto used to determine the "FLEX" parameter, already mentioned with reference to the known art and that will be briefly described herein for a more complete explanation.

In particular, said apparatus for measuring the first two dynamic parameters of a boot consists of an outer case, defining within it a chamber in which the experimental tests are carried out.

The internal chamber is provided with a support plate on which is firmly mounted the sole of the boot to be tested so as to prevent it from shifting in any direction but to allow the upper shell to rotate freely with respect to the lower shell.

Inside the boot is inserted a rigid prosthesis, the upper portion of which is connected to a mechanical arm operated from outside through relative drive and control means; by operating on said mechanical arm, the prosthesis, and therefore the upper shell of the boot, is forced to bend forward, that is, to decrease the width of the angle between the upper shell and the lower shell.

During a complete operating cycle, which includes the rotation of the upper shell from a neutral position to a maximum bending position toward the lower shell and the return to the original neutral position through a rotation in a reverse direction, relative sensors continually measure the value of the bending moment applied to the prosthesis on the basis of the bending angle of the upper shell. In particular, it was decided to consider a bending cycle having preferably an angular amplitude included between −5° and +15° with respect to the neutral position, conditions that, based on tests carried out on the ski slope with professional skiers, appear to accurately represent the ski run conditions.

The data detected from a complete cycle are shown in a graph: as can be seen in FIG. 1, the trend is that of a hysteresis cycle, comprising a first curve F, which corresponds to the bending phase, and a second curve D corresponding to the ensuing relaxation phase.

Finally, from the graph so obtained it is possible to gather the values of the stiffness S and progression P parameters, as will be explained later. However, in order to make the measurements of the stiffness S and progression P parameters repeatable and homogeneous for different types of boots, it was decided to adopt a detection protocol that includes the following steps:

a) a rigid prosthesis, preferably made of silicone, is inserted into the boot to be tested; the upper end of the prosthesis is made integral with a mechanical arm that will exert on the boot the load necessary for carrying out the test;

b) the boot, preferably the right one and of size 265, is then fastened inside the chamber, locking it firmly through the sole to an internal support plate, preventing in this manner any movement of the lower shell but allowing the upper shell to rotate freely with respect to the lower shell;

c) the boot is then allowed to condition at the test temperature (−5° C.), preferably with the clamping levers completely open, for at least three hours: in this manner it is possible to carry out the test at the temperature of actual use, taking into due account the increased stiffness of the materials that takes place with the progressive lowering of the temperature;

d) subsequently, all the levers are clamped with a predetermined force and, by activating the mechanical arm, the inclination of the prosthesis is adjusted so that the load sensed by the cell is close to zero, thus defining the neutral position and the corresponding neutral angle;

e) at the completion of the formal procedure, the test is started, consisting of subjecting the boot, through the mechanical arm integral with the internal prosthesis, to 300 complete cycles at a rate of 15 cycles/minute, between an inclination of the upper shell with respect to the lower shell of −5° and an inclination of +15°, progressively recording the values of the bending moment applied in Nm with respect to the angle of inclination reached.

Figure 2:
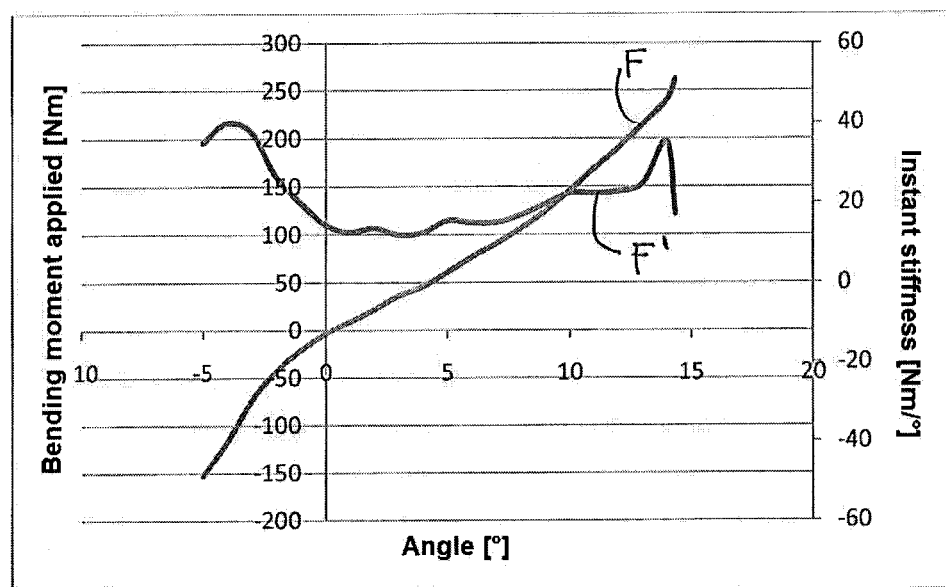

The stiffness parameter S is calculated by determining the slope F' of the bending curve F (that is, the instant stiffness) at a reference angle α, which is conventionally assumed to be equal to 5° (FIG. 2).

In practice, therefore, the stiffness S of the boot will be:

$$S=K_{5°}=(M_{6°}-M_{4°})/2°$$

where M indicates the bending moment applied to obtain the bending angle given in the subscript.

The stiffness parameter S is thus measured in Nm/°.

After having determined reference values for the S parameter, it is then possible to express the stiffness of a boot on the basis of the S parameter measured according to the above procedure, as shown in the following table.

| STIFFNESS S [Nm/°] | Assigned code |
| --- | --- |
| between 24 and 27 | VERY STIFF - A4 |
| between 21 and 24 | STIFF - A3 |
| between 18 and 21 | MEDIUM - A2 |
| between 15 and 18 | PLIABLE - A1 |

Preferably, the reference parameters are determined by carrying out the test on a representative sample of boots having a different stiffness, being capable of meeting the requirements of different skiing disciplines and/or the requirements of the user. The stiffness parameter associated with each boot was determined, measuring in this manner a range of values that can be assumed from the parameter. The above table was thus defined by properly subdividing the whole range into subclasses.

Clearly, the reference values are purely approximate, and may be modified in time, or more classes and subclasses may be added as the technology evolves and on the basis of further developments of new boot models, new skiing disciplines and different methods of measurement.

As mentioned above, the "progression" parameter P, which represents the increasing stiffness during a bending cycle, can be measured during the same tests carried out for the stiffness S test; in fact, in actual practice, the progression P is measured as the adimensional relationship between the slope of the curve representing the bending moment on the basis of the bending angle, at a bending angle β conventionally assumed to be 10° and the slope of the same curve at a bending angle α of 5° (equivalent to the value of S).

Operatively, therefore, it is necessary to estimate the slope of the bending curve at 10°:

$$K_{10°}=(M_{11°}-M_{9°})/2°$$

where M indicates the bending moment applied to obtain the bending angle given in the subscript, and then to calculate the value of P in the following manner:

$$P=K_{10°}/K_{5°}.$$

Thus, the P parameter is adimensional. By predetermining reference ranges for the P parameter, it is possible to determine the progression of a boot by comparing the P value obtained experimentally with the reference ranges.

The reference values for the P parameter can be obtained by determining experimentally the same parameter for different types of boots, defining a range of values that can be assumed and appropriately dividing said range into subclasses, so as to make it possible to have the following reference table:

| PROGRESSION P [-] | Assigned code |
| --- | --- |
| greater than 1.8 | cubic - B3 |
| between 1.4 and 1.8 | quadratic - B2 |
| between 1 and 1.4 | linear - B1 |

As mentioned above for the previous parameter, the reference values are purely approximate, and may be modified in time, or more classes and subclasses may be added as the technology evolves and on the basis of further developments of new boot models, new skiing disciplines and different methods of measurement.

For what concerns, instead, the rebound parameter R, it was necessary to provide a new apparatus 1 for the experimental measurement of the same.

Said apparatus 1 for measuring the rebound R includes essentially an outer case, preferably metallic, comprising an access opening and an internal chamber, in which is placed the boot 5 to be tested, and a command and control assembly for operating said apparatus, said assembly itself being controlled through an external control interface (not shown).

Within the chamber are provided means of known type (not shown) for cooling the air inside the chamber, as, in this case too, the tests are preferably carried out at a temperature of −5° C.

Figure 3:
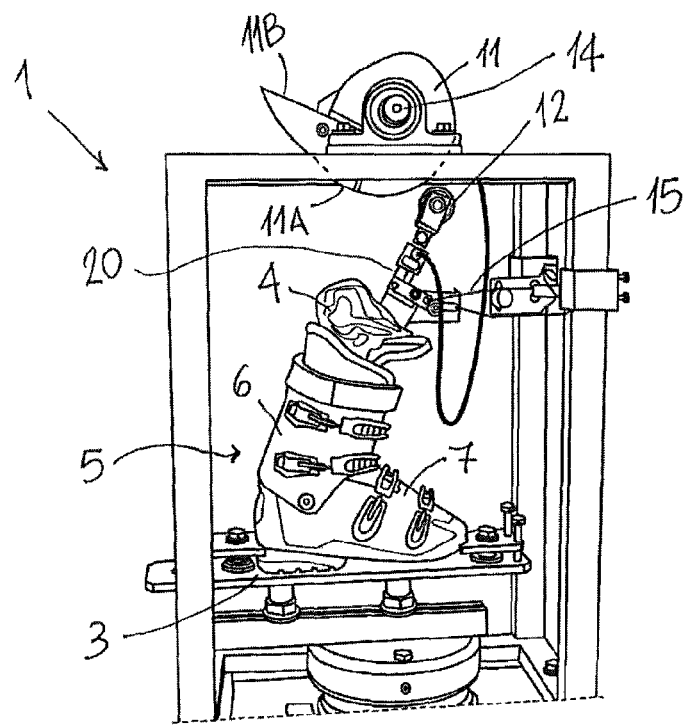
FIG. 3 illustrates a new apparatus for determining a further parameter for the dynamic characterization of a boot.
Figure 4:
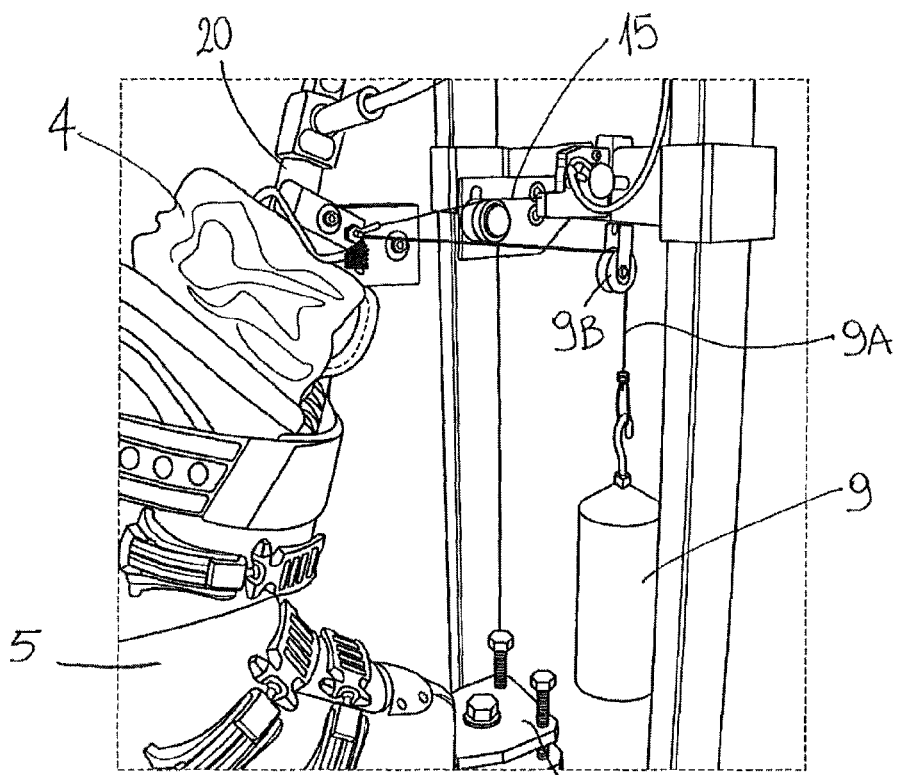
FIG. 4 shows a detail of the apparatus of the previous figure.

FIGS. 3 and 4 illustrate the inside of the apparatus 1, in which is provided a support plate 3 on which is solidly mounted the sole of the boot 5 to be tested; this way, the movement of the bottom shell 7 is prevented, while the upper shell 6 remains free to rotate.

A prosthesis 4 is inserted into the boot 5; said prosthesis 4 is firmly fixed to an elongate element 20 that projects from the upper end of the prosthesis, and is provided, at the top, with an anti-friction element 12, such as a ball bearing. Said ball bearing 12 is suitable to cooperate with the outer surface 11A of a cam-shaped bending induction means 11 mounted above it. The distance between the centre of rotation of the cam 11 and the centre of rotation of the bearing 12 is predefined and, at the start of the test, it is necessary to make sure that this distance is respected (FIG. 5B).

Preferably, to guarantee that the measurement is as accurate as possible and to avoid the possibility that the values measured are distorted by inertial forces caused by the materials making up the boot, a preload is applied to the prosthesis 4, preferably by connecting a weight 9 to the elongate element 20 near the top end of the prosthesis 4, by means of a relative cable 9A cooperating with a pulley 9B. In particular, it was found that a preload of 5 kg makes it possible to obtain the desired result.

The operation of the device for measuring the rebound R is as follows: the cam 11 is rotatably mounted on a driven shaft 14 connected, for example through a chain drive and gear wheels, to an external motor (not shown), that drives it at a certain rotation speed.

The rotation movement of the cam 11 is free (FIG. 5C) until the outer surface 11A of the same comes into contact with said bearing 12 (FIG. 5D): the outer surface 11A of the cam 11 is suitably shaped so that, cooperating with the bearing 12, a progressive load is applied to the prosthesis 4, so as to force it to bend forward to the maximum bending position (FIG. 5E), which conventionally corresponds to a 10° bending angle of the upper shell 6 toward the lower shell 7 with respect to the initial neutral position.

At this point, the outer surface of the cam 11A comprises an abrupt discontinuity 11B that allows the prosthesis 4 to deflect and freely return to the initial position.

A speed detection means 15, such as for example a wire potentiometer, is suitably connected to the upper shell 6; through said means it is possible to detect the return speed of the upper shell from the maximum bending position to the neutral position.

The return parameter R is thus a speed and therefore it is preferably measured in cm/s.

In particular, said wire potentiometer 15 has an end connected to a fixed reference point integral with the outer case, and the opposite end is connected to the elongate element 20 integral with the upper shell 6.

Figure 5A:
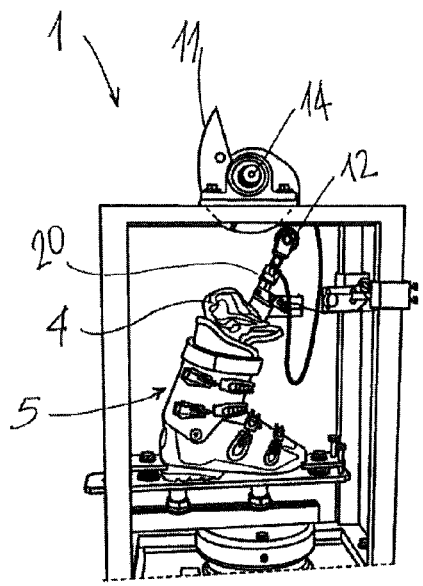
FIGS. 5A, 5B, 5C, 5D, 5E and 5F show the steps of the procedure for measuring a parameter through the use of the apparatus of FIG. 3.
Figure 5B:
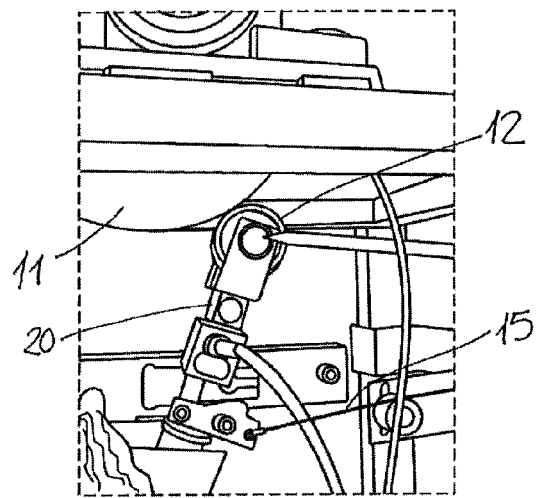
Figure 5C:
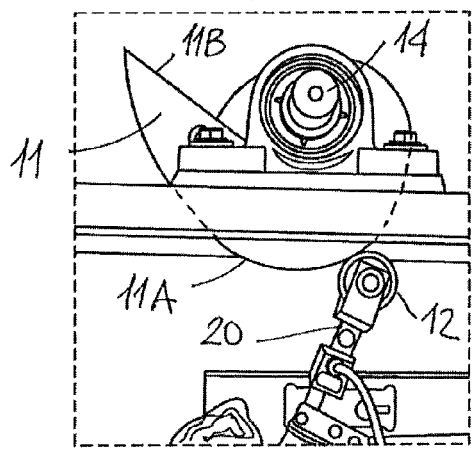
Figure 5D:
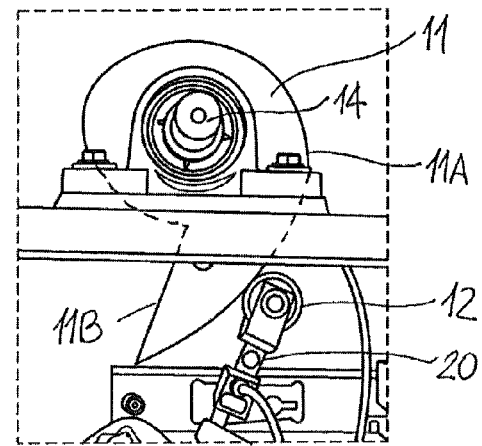
Figure 5E:
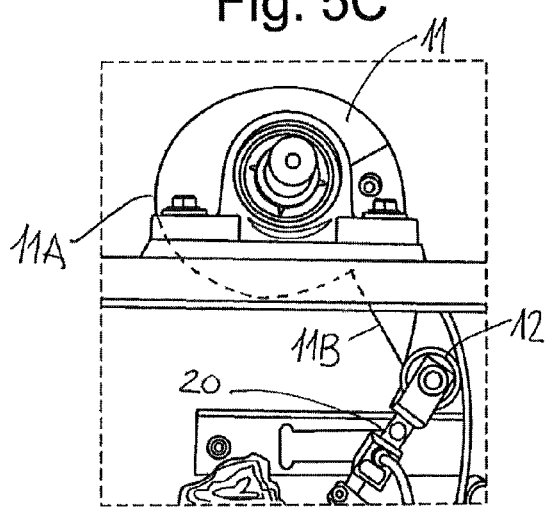
Figure 5F:
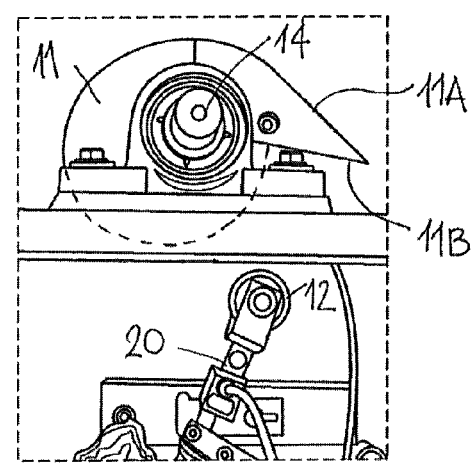

In order to ensure the repeatability of the measurement of the rebound parameter R for different types of ski boots, it was decided to adopt a measurement protocol that comprises the following steps:

a) insertion of the prosthesis 4 into the boot 5 and fastening the boot through its sole to the support plate 3 of the measurement apparatus 1;

b) allowing the boot 5, preferably the right one and of size 265, to condition in the internal chamber of the apparatus 1 at the testing temperature (−5° C.) for at least three hours, preferably leaving the clamping levers of the boot 5 open (FIG. 5A);

c) tightening the clamping levers of the boot 5 with a predetermined force and applying the preload 9 to the prosthesis 4, ensuring that the centre of rotation of the bearing 12 is set at the foreseen distance from the centre of rotation of the cam 11 (FIG. 5B);

d) starting the test, putting the cam 11 (FIG. 5C) into rotation through the driven shaft 14, and consequently bending the upper shell 6 toward the lower shell 7 (FIG. 5D); the tests consists of five complete cycles of rotation of the cam 11 at a speed of 11 rpm. The value of the rebound parameter R will thus be the same as the average between the five speed values detected by the detection means 15 during the test.

By presetting the reference classes, defined as the limit values of the R parameter, it is possible to determine the rebound R of a ski boot by simply comparing the experimental value of R with the reference classes.

For this parameter, too, as for the previous ones, the reference values for the R parameter can be obtained by experimentally determining the same parameter for different types of ski boots, defining a range of values that can be assumed and suitably dividing said range into subclasses, so as to obtain the following reference table:

| REBOUND R [cm/s] | ASSIGNED CODE |
|---|---|
| greater than 126 | FAST - C1 |
| between 111 e 125 | MEDIUM - C2 |
| between 90 e 110 | SLOW - C3 |

In this case, too, the reference values are purely approximate, and may be modified in time, or more classes and subclasses may be added as the technology evolves and on the basis of further developments of new boot models, new skiing disciplines and different methods of measurement.

Laboratory research and measurements carried out on different types of ski boots have made it possible to obtain the following reference table, which correlates the assumed values of the S, P and R parameters with specific sport applications:

| Family | Application | Stiffness S [Nm/°] | Progression P [-] | Rebound R [cm/s] |
|---|---|---|---|---|
| RACE | Competition | A4 | B3 | C1 |
| FREE RIDE | Off-piste | A2 | B3 | C1 |
| PRO | Amateur competition | A3 | B2 | C1 |
| AGGRESSIVE FRONTSIDE | Expert skier | A3 | B2 | C2 |
| SIDE COUNTRY | Off-piste amateur | A2 | B2 | C2 |
| PARK & PIPE | Somersaults, acrobatic | A2 | B2 | C3 |
| ALL MOUNTAIN | Beginner/ Tourist | A2 | B1 | C3 |
| SPORT PERFORMANCE | Beginner/ Tourist | A2 | B1 | C3 |

The values assumed from the parameters of stiffness S, progression P and rebound R, if taken together, define a sort of "dynamic identity card" of the ski boot. Consequently, by comparing the values obtained for a boot with the reference values given in the above table it is possible to immediately recognize the dynamic behaviour of the same.

In other words, summarizing, the method for determining the dynamic characteristics of a boot according to the present invention comprise the following steps:
- a) defining at least a first, second and third parameter, suitable to represent the dynamic characteristics of a ski boot;
- a') predetermining the reference values of said parameters on a sample of ski boots having different dynamic behaviours;
- b) experimentally determining the value of said first parameter for said ski boot;
- c) experimentally determining the value of said second parameter for said ski boot;
- d) experimentally determining the value of said third parameter for said ski boot;
- d') comparing the values of said first, second and third parameter detected in said steps b) to d) with the reference parameters determined in step a');
- e) defining the type of dynamic behaviour of the ski boot based on the combination of the values measured in said steps b) to d) with respect to the reference parameters determined in step a').

The above table indicates the dynamic characteristics required of a ski boot to guarantee optimum performance for each specific discipline. Advantageously, on the package of any new ski boot will be marked, for each of the three parameters considered S, P and R, the corresponding code of the relative subclass, for example in the form of an icon. A similar icon may also be applied on the boot itself.

In this manner it is possible to immediately view the characteristics of a boot and correctly evaluate its dynamic behaviour. In other words, for example, if the parameters measured experimentally for one boot are, respectively, S included between 24 and 27 Nm/° (that is included in the range denominated A4), P greater than 1.8 (B3 range) and R greater than 126 cm/s (range C1), then it is possible to establish if the dynamic behaviour of that boot corresponds to the dynamic behaviour of a competition boot for professionals.

In conclusion, it is evident that a method for determining the dynamic characteristics of a ski boot according to the present invention achieves the purposes and advantages initially foreseen.

In fact, a simple method has been achieved that on one hand offers particular advantages to manufacturers of ski boots, so that they may verify if a boot designed for a specific discipline or skill level meets the preset dynamic requirements and, if this is not the case, they may introduce appropriate technical modifications until the boot meets all the dynamic requirements given in the following reference table.

| Family | Application | Stiffness S [Nm/°] | Progression P [-] | Rebound R [cm/s] |
|---|---|---|---|---|
| RACE | Competition | A4 | B3 | C1 |
| FREE RIDE | Off-piste | A2 | B3 | C1 |
| PRO | Amateur competition | A3 | B2 | C1 |
| AGGRESSIVE FRONTSIDE | Expert skier | A3 | B2 | C2 |
| SIDE COUNTRY | Off-piste amateur | A2 | B2 | C2 |
| PARK & PIPE | Somersaults, acrobatic | A2 | B2 | C3 |
| ALL MOUNTAIN | Beginner/ Tourist | A2 | B1 | C3 |
| SPORT PERFORMANCE | Beginner/ Tourist | A2 | B1 | C3 |

On the other hand, said method is certainly useful for the sellers (or also for the users), who will be able to guide in the choice of a ski boot most suitable for one's skiing discipline and skill level. For example, if a skiing beginner wants to buy a new pair of ski boots, the seller will guide him/her in the choice of the boots by reading the values drawn from the parameters of dynamic behaviour, possibly represented in the form of a schematic icon, and comparing them with those of the above reference table, to understand immediately and intuitively if that pair of boots is suitable for the requirements of the customer.

Moreover, said method of determining the dynamic characteristics is based on three parameters, considered to be the most representative, that can be univocally determined experimentally through measurements obtained with easily repeatable procedures.

Said three parameters express in fact as many intuitive characteristics that enable the user to immediately identify the type of ski boot that best fits his/her needs. Moreover, advantageously, said parameters are marked in the form of icons on the package of the boots and/or on the boots themselves in a manner that can be easily and quickly interpreted.

Naturally, the present invention is amenable to numerous applications, modifications or variants without thereby departing from the scope of patent protection, as defined by the appended claims.

Moreover, the materials and equipment used to realize the present invention, as well as the shapes and dimensions of the individual components, may be the most suitable to meet the specific requirements.

The invention claimed is:

1. A method for determining the dynamic characteristics of a ski boot comprising an upper shell and a lower shell, comprising:
- a) defining at least a first, second and third parameter, (S), (P) (R) which represent dynamic characteristics of a ski boot;
- b) experimentally determining the value of said first parameter for said ski boot;
- c) experimentally determining the value of said second parameter for said ski boot;
- d) experimentally determining the value of said third parameter for said ski boot;
- e) defining a dynamic behaviour of said ski boot based on a combination of the values measured in said steps b) to d), wherein:
said first parameter (S) is a bending moment, measured in Nm/°, to be applied to bend an upper shell of the ski boot to a first angle α relative to said lower shell starting from a neutral position;
said second parameter (P) adimensionally expresses a stiffness increase during the bending from a neutral position to a maximum bending position of the upper shell relative to a lower shell; and
said third parameter (R) expresses a speed to which the upper shell returns to the neutral position from a maximum bending position relative to the lower shell.

2. The method for determining the dynamic characteristics of a ski boot according to claim 1, further comprising:
- a') subsequently to said step a), pre-determining, on a sample of ski boots with different dynamic behaviours, the reference values for said first, second and third parameter; and
- d') comparing the values of said first, second and third parameter measured during said steps b) to d) with the reference parameters determined during the step a') to define the dynamic behaviour of the ski boot.

3. The method for determining the dynamic characteristics of a ski boot according to claim 1, wherein:
said second parameter (P) is calculated as a ratio between a bending moment to be applied to bend said upper shell relative to said lower shell of a second angle $\beta > \alpha$ and a bending moment to be applied to bend said upper shell relative to said lower shell of said first angle $\alpha$.

4. The method for determining the dynamic characteristics of a ski boot according to claim 3, wherein said first angle $\alpha$ is equal to 5°.

5. The method for determining the dynamic characteristics of a ski boot according to claim 4, wherein said second angle is equal to 10°.

6. The method for determining the dynamic characteristics of a ski boot according to claim 5, wherein a value of said first parameter (S) between 24 and 27 Nm/°, a value of said second parameter (P) greater than 1.8, and a value of said third parameter (R) greater than 126 cm/s define the dynamic behaviour of said ski boot corresponding to a behaviour of a ski boot suitable for professional ski race.

7. The method for determining the dynamic characteristics of a ski boot according to claim 5, wherein a value of said first parameter (S) between 18 and 21 Nm/°, a value of said second parameter (P) greater than 1.8, and a value of said third parameter (R) greater than 126 cm/s define the dynamic behaviour of said ski boot corresponding to a behaviour of a ski boot suitable for free-ride.

8. The method for determining the dynamic characteristics of a ski boot according to claim 5, wherein a value of said first parameter (S) between 21 and 24 Nm/°, a value of said second parameter (P) between 1.4 and 1.8, and a value of said third parameter (R) greater than 126 cm/s define the dynamic behaviour of said ski boot corresponding to a behaviour of a ski boot suitable for amateur ski race.

9. The method for determining the dynamic characteristics of a ski boot according to claim 5, wherein a value of said first parameter (S) between 21 and 24 Nm/°, a value of said second parameter (P) between 1.4 and 1.8, and a value of said third parameter (R) between 111 and 125 cm/s define the dynamic behaviour of said ski boot corresponding to a behaviour of a ski boot suitable for expert skiers.

10. The method for determining the dynamic characteristics of a ski boot according to claim 5, wherein a value of said first parameter (S) between 18 and 21 Nm/°, a value of said second parameter (P) between 1.4 and 1.8 and a value of said third parameter (R) between 111 and 125 cm/s define the dynamic behaviour of said ski boot corresponding to a behaviour of a ski boot suitable for side-country.

11. The method for determining the dynamic characteristics of a ski boot according to claim 5, wherein a value of said first parameter (S) between 18 and 21 Nm/°, a value of said second parameter (P) between 1.4 and 1.8, and a value of said third parameter (R) included between 90 and 110 cm/s define the dynamic behaviour of said ski boot corresponding to a behaviour of a ski boot suitable for park and pipe.

12. The method for determining the dynamic characteristics of a ski boot according to claim 5, wherein a value of said first parameter (S) between 18 and 21 Nm/°, a value of said second parameter (P) between 1 and 1.4, and a value of said third parameter (R) between 90 and 110 cm/s define the dynamic behaviour of said ski boot corresponding to a behaviour of a ski boot suitable for beginners/touring.

13. An apparatus for determining a dynamic behaviour parameter of a ski boot including an upper shell and a lower shell, said parameter expressing a rebound of the upper shell relative to the lower shell from a maximum bending position to a neutral position, comprising an external case, inside which is housed a chamber in which is placed said ski boot, and a command and control assembly for operating said apparatus, said apparatus including an air cooler for said chamber means to bend said upper shell, and a detector for detecting the return speed of said upper shell from said maximum bending position to said neutral position.

14. The apparatus for determining the parameter according to claim 13, wherein said speed detector comprise a wire potentiometer having an end associated to a fixed reference point integral to said external case and an opposite end integral with said upper shell.

15. The apparatus for determining a parameter according to claim 13 or 14, wherein said means to bend said upper shell comprise a cam rotatably mounted on a driven shaft, said cam comprising an outer surface shaped to cooperate with an anti-friction element integral with the upper shell to progressively force said upper shell to a maximum bending position, at which said outer surface comprises a discontinuity that allows said upper shell to freely return to said neutral position.

* * * * *